United States Patent
Stoller et al.

(10) Patent No.: US 9,920,001 B2
(45) Date of Patent: Mar. 20, 2018

(54) METHOD FOR ENHANCING THE RATE OF THE FORMATION OF THE REACTION PRODUCT OF A CARBOXYLIC ACID AND UREA VIA ACID ADDITION

(71) Applicant: Stoller Enterprises, Inc., Houston, TX (US)

(72) Inventors: Jerry Stoller, Houston, TX (US); Ritesh Sheth, Friendswood, TX (US)

(73) Assignee: Stoller Enterprises, Inc., Houston, TX (US)

( * ) Notice: Subject to any disclaimer, the term of this patent is extended or adjusted under 35 U.S.C. 154(b) by 27 days.

(21) Appl. No.: 14/984,049

(22) Filed: Dec. 30, 2015

(65) Prior Publication Data

US 2016/0185715 A1    Jun. 30, 2016

Related U.S. Application Data

(60) Provisional application No. 62/098,180, filed on Dec. 30, 2014.

(51) Int. Cl.
*C07C 273/18* (2006.01)
*A01N 47/28* (2006.01)

(52) U.S. Cl.
CPC ........ *C07C 273/1863* (2013.01); *A01N 47/28* (2013.01)

(58) Field of Classification Search
None
See application file for complete search history.

(56) References Cited

U.S. PATENT DOCUMENTS

| | | | |
|---|---|---|---|
| 6,040,273 A * | 3/2000 | Dean | C07C 275/50 504/327 |
| 6,448,440 B1 | 9/2002 | Dean | |
| 6,710,085 B2 | 3/2004 | Dean | |
| 8,846,903 B2 | 9/2014 | Bialer et al. | |

FOREIGN PATENT DOCUMENTS

DE    87780    11/1972

OTHER PUBLICATIONS

Lewis Acids [downloaded from the archived website https://web.archive.org/web/20090410060109/http://wps.prenhall.com/wps/media/objects/3312/3392119/blb1611.html on Jan. 12, 2017].*
Röper et al., "Acylation and Alkylation", Ullmann's Encyclopedia of Industrial Chemistry 1: 393-437 (Jun. 2000).*
Farag et al., "Preparation, thermogravimetric and spectroscopic studies of transition metal complexes of Schiff-base condensation ligands", Egyptian J Chem 49(2): 157-168 (2006).*
Wikipedia entry for Schiff bases—2017.*
Stoughton; Roger W.; "Diacylureas. I. Preparation and Properties of Diacylureas Derived From Normal Aliphatic Acids", Journal of Organic Chemistry 2(6), pp. 514-521, 1938, Abstract.

* cited by examiner

*Primary Examiner* — Robert A Wax
*Assistant Examiner* — Thor Nielsen
(74) *Attorney, Agent, or Firm* — Yancy IP Law, PLLC

(57) ABSTRACT

The present invention is directed to a method for enhancing the rate of formation of the reaction products of a carboxylic acid and a urea having the formula:

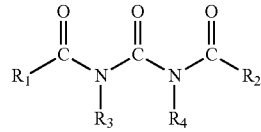

where $R_1$, $R_2$, $R_3$ and $R_4$ are the same or different and are selected from the group consisting of hydrogen, substituted and unsubstituted alkyl, allyl, vinyl and alkoxyl groups having from 1-6 carbon atoms, substituted and unsubstituted phenyl groups and the halides. The rate of formation is enhanced by adding acid to a solution including the carboxylic acid and the urea. Preferably, the reaction product of the present invention is N,N'-diformylurea or N,N'-diacetylurea. These reaction products, e.g., diformylurea, have been found to produce significantly improved growth in a variety of agricultural products when applied to the seed, to the surrounding soil or to the foliage of the emerging plant.

13 Claims, 7 Drawing Sheets

METHOD FOR ENHANCING THE RATE OF THE FORMATION OF THE REACTION PRODUCT OF A CARBOXYLIC ACID AND UREA VIA ACID ADDITION

CROSS-REFERENCE TO RELATED APPLICATIONS

This application claims the benefit, under 35 U.S.C. 119(e), of U.S. Provisional Application No. 62/098,180 filed Dec. 30, 2014, the contents of which are incorporated herein by reference.

BACKGROUND OF THE INVENTION

1. Field of the Invention

The present invention generally relates to a method for enhancing the rate of the formation of the reaction product of a carboxylic acid and a urea, such as a substituted urea, via acid addition. The reaction product may be used as an agricultural product to improve plant growth. More specifically, the present invention is directed to the addition of at least one acid to a solution including the carboxylic acid and urea.

2. Description of the Background

Urea, being approximately 46% by weight nitrogen, has long been preferred as a nitrogen source for fertilizing soils to stimulate plant growth. However, urea suffers from high ammonia losses when used in the presence of moisture. This disadvantage effectively restricted the use of urea for many years. It is believed that these losses are caused by the hydrolysis of urea in the presence of moisture and the enzyme urease. The addition of a water soluble salt to aqueous solutions of urea has been suggested as a means for reducing ammonia volatilization. See U.S. Pat. No. 4,500,335. While substituted ureas are also known, e.g., diphenylurea, they have found little agricultural use.

Diacyl ureas are a product formed by the reaction of a carboxylic acid and a urea. For example, diformylurea (DFU) is formed by the reaction of 2 equivalent of formic acid with urea over 5-7 days. The by-product of the reaction is water.

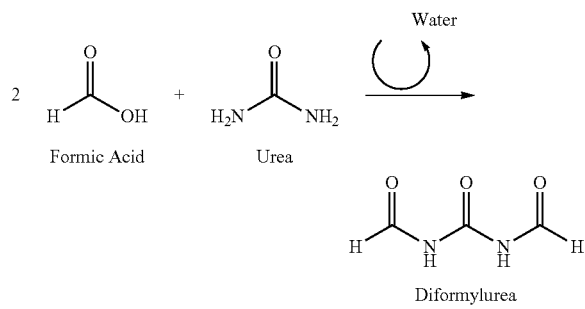

While activity with this formulation has been good, improvements in performance are desirable. As such, previous formulations have included the addition of various compounds to the diacyl urea formulation prior to use. For example, potassium hydroxide and formate may be added to the formulation. The addition of potassium hydroxide may be included to adjust the pH of the formulation, see U.S. Pat. No. 6,710,085, U.S. Pat. No. 6,448,440, and U.S. Pat. No. 6,040,273, the contents of which are expressly incorporated herein by reference. However, a formulation that does not require the addition of such compounds would be advantageous.

SUMMARY OF THE INVENTION

The present invention is directed to a method for enhancing the rate of formation of the reaction product of a carboxylic acid and a urea, including mono- and di-substituted ureas, by the addition of at least one acid to a solution containing the carboxylic acid and the urea. "Acid" may refer to a single acid or combination of acids that include both inorganic and organic acids. "Inorganic acids" may consist of, but are not limited to, both Bronsted and Lewis acids such as sulfuric acid, sulfamic acid, hydrochloric acid, hydrobromic acid, hydrofluoric acid, nitric acid, phosphoric acid, polyphosphoric acid, and metal halides (i.e. $TiCl_4$, $BF_3$, $MgBr_2$, $SnCl_4$, $FeCl_3$, $AlCl_3$, etc.). "Organic acids" may consist of, but are not limited to, alkyl and aryl sulfonic acids, amino acids, trihaloalkyl acids, and organo titanates. In a preferred embodiment, the reaction product of the present invention comprises an N,N'-di-substituted urea having the formula:

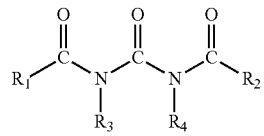

where $R_1$, $R_2$, $R_3$ and $R_4$ are the same or different and are selected from the group consisting of hydrogen, substituted and unsubstituted alkyl, allyl, vinyl and alkoxyl groups having from one to six carbon atoms, substituted and unsubstituted phenyl groups and the halides.

The reaction products of the present invention, most preferably N,N'-diformylurea, has been found to produce enhanced growth in plants when used in a variety of ways. These reaction products, most preferably diformylurea, produce enhanced growth when applied to seeds prior to planting, when applied to the soil surrounding the plant at or after planting or when applied to the foliage of the plant, e.g., at the three leaf stage of growth.

BRIEF DESCRIPTION OF THE DRAWINGS

The features and advantages of the present invention will become apparent from the following detailed description of a preferred embodiment thereof, taken in conjunction with the accompanying drawings, in which.

DETAILED DESCRIPTION OF THE PREFERRED EMBODIMENT

Figure 1:
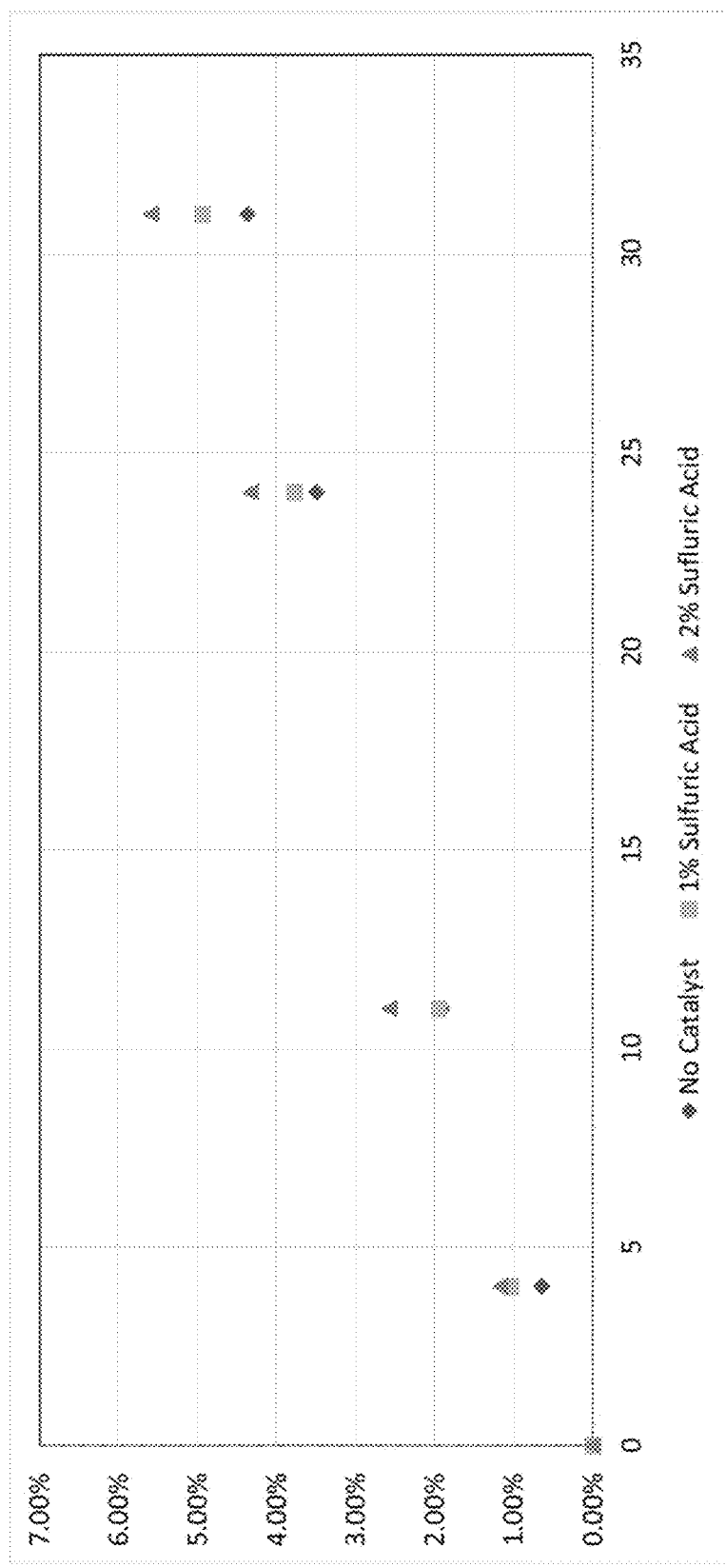
FIG. 1 is a graph showing DFU formation at 30° C. with varying concentrations of sulfuric acid in accordance with the present invention.

The present invention is directed to a method for making a reaction product with enhanced rate of formation including: 1) providing a solution including a carboxylic acid and a urea and 2) adding at least one acid to said solution to form the reaction product. In a preferred embodiment, the method includes a solution only containing said carboxylic acid, said urea and said at least on acid. In one embodiment, the at least one acid is added to provide a solution including 0.1-20 wt. % acid. Alternatively, the at least one acid is added to provide a solution including 0.1-10 wt. % acid. Additionally, alternate embodiments would include adding the at least one acid to provide a solution including 1-20 wt. % acid, 1-10 wt. % acid, or 1-6 wt. % acid. The addition of at least one acid improves the rate of formation of the reaction product. Furthermore, it has been found that the rate of photosynthesis to plants subjected to the reaction product may be greatly increased. Additionally, a greater decrease in Reactive Oxidative Species (ROS), a measurement of stress, is also observed. Furthermore, a formulation for enhancing plant growth may include at least one solvent and the reaction product, wherein said formulation does not contain any pH modifiers. The formulation may be prepared by dissolving the reaction product in at least one organic solvent such as, but not limited to, dimethylsulfoxide (DMSO) and N-methylpyrrolidone (NMP), which has demonstrated greater yield when applied to both monocots and dicots. These reaction products may be easily prepared and have significant agricultural uses because of their perceived biological activity. In fact, it is believed that these reaction products, specifically N,N'-diformylurea (DFU), will enhance the growth of a variety of agricultural crops when applied to the seeds, surrounding soil or foliage.

The reaction products of the present invention have the general formula:

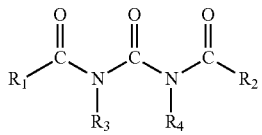

where $R_1$, $R_2$, $R_3$ and $R_4$ are the same or different and are selected from the group consisting of hydrogen, substituted and unsubstituted alkyl, allyl, vinyl and alkoxyl groups having from 1-6 carbon atoms, substituted and unsubstituted phenyl groups and the halides. These reaction products are prepared by reacting a carboxylic acid having the formula RCOOH where R is selected from the group consisting of hydrogen, substituted and unsubstituted alkyl, allyl, vinyl and alkoxyl groups having from 1-6 carbon atoms, substituted and unsubstituted phenyl groups and the halides. Preferably, R is selected from the group consisting of hydrogen and unsubstituted alkyl groups having from 1-3 carbon atoms. Exemplary acids include formic acid, acetic acid, propionic acid, butyric acid, valeric acid, caproic acid, heptanoic acid, and citric acid. The presently most preferred acids are formic or acetic acid. These carboxylic acids are reacted with a substituted or unsubstituted urea having the formula $(NHR')_2CO$ where each R' is the same or different and is selected from the group consisting of hydrogen, substituted and unsubstituted alkyl groups having from 1-6 carbon atoms, substituted and unsubstituted alkoxyl groups having from 1-6 carbon atoms, substituted and unsubstituted phenyl groups and the halides. The preferred reactant is unsubstituted. After the carboxylic acid and urea are dissolved, acid is added to the solution. In one embodiment of the present invention, the solution may include 0.1-20 wt. % acid. In an alternate embodiment of the present invention, the solution may include 0.1-10 wt. % acid.

In its most preferred embodiment, the present invention comprises the reaction product of urea and formic acid, i.e., N,N'-diformylurea, having the following formula:

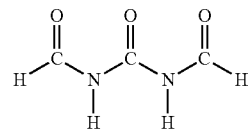

In this reaction, formic acid reacts with one hydrogen on each of the urea nitrogens to produce N, N'-diformylurea. Accordingly, it is preferred that the reaction mixture comprise about 2 moles of carboxylic acid for each mole of urea. The reaction of the present invention will proceed throughout a wide range of temperatures, e.g. from about 10° C. to about 140° C., restricted only by the boiling points of the reactants and products. While heat may be added by any conventional means to speed the rate of these reactions, it has been found that the methods of the present invention may conveniently be performed in a temperature range from about 15° C. to about 70° C., preferably at temperatures, i.e., from about 20° C. to about 50° C. It is preferred that the reaction mixture be stirred until clear and then permitted to remain quiescent until crystals of the reaction product have formed.

It is believed that these reaction products will be biologically active as a result of the similarity of their skeletal structure, i.e., the nitrogen-carbon-oxygen skeleton, with the alternating double bond structure of these same elements in a variety of synthetic and naturally occurring biological molecules. Thus, it is believed that these reaction products, e.g., N,N'-diformylurea, will find a variety of biological uses. These reaction products may be used to produce, not only the improved plant growth shown herein, but with the substitution of appropriate functional groups or bulky substituents, a variety of effective algaecides, herbicides, fungicides or pesticides may be produced.

It is believed that the reaction products claimed herein, particularly N,N'-diformylureas, may mimic plant growth hormones and/or plant growth regulators based upon the similarity of their skeletal structure to a variety of biologically active compounds. Common to all biologically active molecules in this class is a core structure including both alternating double bonds and alternating carbon to nitrogen bonds. These structures are common in all synthetically produced and naturally occurring biologically active molecules, e.g., cytokinens, substituted uracils, methylguanine and the like. While adenine and guanine have a fused ring structure, cytosine, thymine and uracil exhibit the same structures as pyrimidines. Because the N,N'-di-substituted ureas of the present invention, e.g., diformylurea, are linear, they can conform to the shapes of these biological molecules. While this conformation is not exact, it is believed that this feature will facilitate the biological activity of these molecules.

The reaction products of the present invention, specifically N,N'-diformylurea, have been used to enhance the growth of plants. In fact, it has been found that improved growth may be obtained by applying diformylurea to the seeds, or to the soil surrounding the plant, or to the foliage of the plant. A single application of diformylurea may produce significantly greater growth in a variety of crops, including wheat, corn, peanuts, soybeans, rice and cotton.

In one method of the present invention, seeds are treated with a formulation including an aqueous and/or organic solution containing the reaction product, such as N,N'-disubstituted, formed from a carboxylic acid and urea in the presence of at least one acid. Seeds may conveniently be soaked in an aqueous solution containing the reaction product for a time from about 2-24 hours. The seeds may be immediately planted or may be dried to produce a seed which has been treated with the reaction product.

While those skilled in the art will be able to prepare a formulation including the reaction product and an aqueous and/or organic solvent of the desired concentration without any pH modifiers for these agricultural uses, it has been found that formulations containing from about 0.001-1.0 M of the reaction product are typically appropriate. Formulations prepared from aqueous and/or organic solvents containing from about 0.001-0.050 M are presently preferred. While these solutions may be applied at any rate desired by those of skill in the art, it has been found that formulations containing aqueous and/or organic solvent of the foregoing concentration provide good results when applied at the rate of about 15-750 ml. per 100 lbs of seed. Alternatively, it is believed that the reaction products of the present invention, typically in formulations including aqueous and/or organic solvents of the foregoing concentrations, may be added to the soil surrounding the seed at planting or after emergence of the plant. In another alternative method, the formulation may be applied by a one-time spraying of the foliage of the emerging plant, preferably at the three leaf stage, with the formulation including an aqueous solvent and the reaction product. Those skilled in the art would be aware that addition of a small quantity of oil and/or surfactant to the formulation including the aqueous solvent sprayed on the foliage will improve the adherence of the reaction product to the leaves and the uptake of the reaction product by the plant. Suitable oils include both saturated and unsaturated oils, alcohols, esters and other compounds having both hydrophobic and hydrophilic functional groups. Exemplary oils comprise the vegetable oils and include sunflower oil and soybean oil. Exemplary biologically acceptable surfactants include the organic polyphosphates, siloxanes, and alcohol ethoxylates. Again, those skilled in the art can determine appropriate concentrations for each desired use. However, formulations including the aqueous and/or organic solvents having the foregoing concentrations are believed to be generally appropriate. These formulations should be applied at a rate sufficient to provide about 1-100 grams of reaction product per acres.

As previously indicated, it is preferred that the reaction products of the present invention are beneficially applied to a plant using a formulation that does not include pH modifiers. Such pH modifiers may include hydroxide-containing compounds, such as potassium hydroxide.

EXAMPLES

Example preparations of N,N'-Diformylurea may be found in U.S. Pat. No. 6,710,085, which is incorporated herein by reference. The reaction mixture may be altered in accordance with the present invention to include 0.1-20 wt. % acid.

Rate Enhancement Examples at Varying Temperatures

Example 1 (No Catalyst)

3.62 grams of urea (60.3 mmol) and 5.78 g of formic acid were combined and heated over a period of 3 h at 30° C. Aliquots were taken out at 5-15 min intervals for analysis. Test was repeated with fresh raw material at 50° C.

Example 2 (1% Sulfuric Acid)

3.62 grams of urea (60.3 mmol), 5.78 g of formic acid, and 0.10 g of 99% sulfuric acid were combined and heated over a period of 3 h at 30° C. Aliquots were taken out at 5-15 min intervals for analysis. Test was repeated with fresh raw material at 50° C.

Example 3 (2% Sulfuric Acid)

3.62 grams of urea (60.3 mmol), 5.78 g of formic acid, and 0.19 g of 99% sulfuric acid were combined and heated over a period of 3 h at 30° C. Aliquots were taken out at 5-15 min intervals for analysis. Test was repeated with fresh raw material at 50° C.

Figure 2:
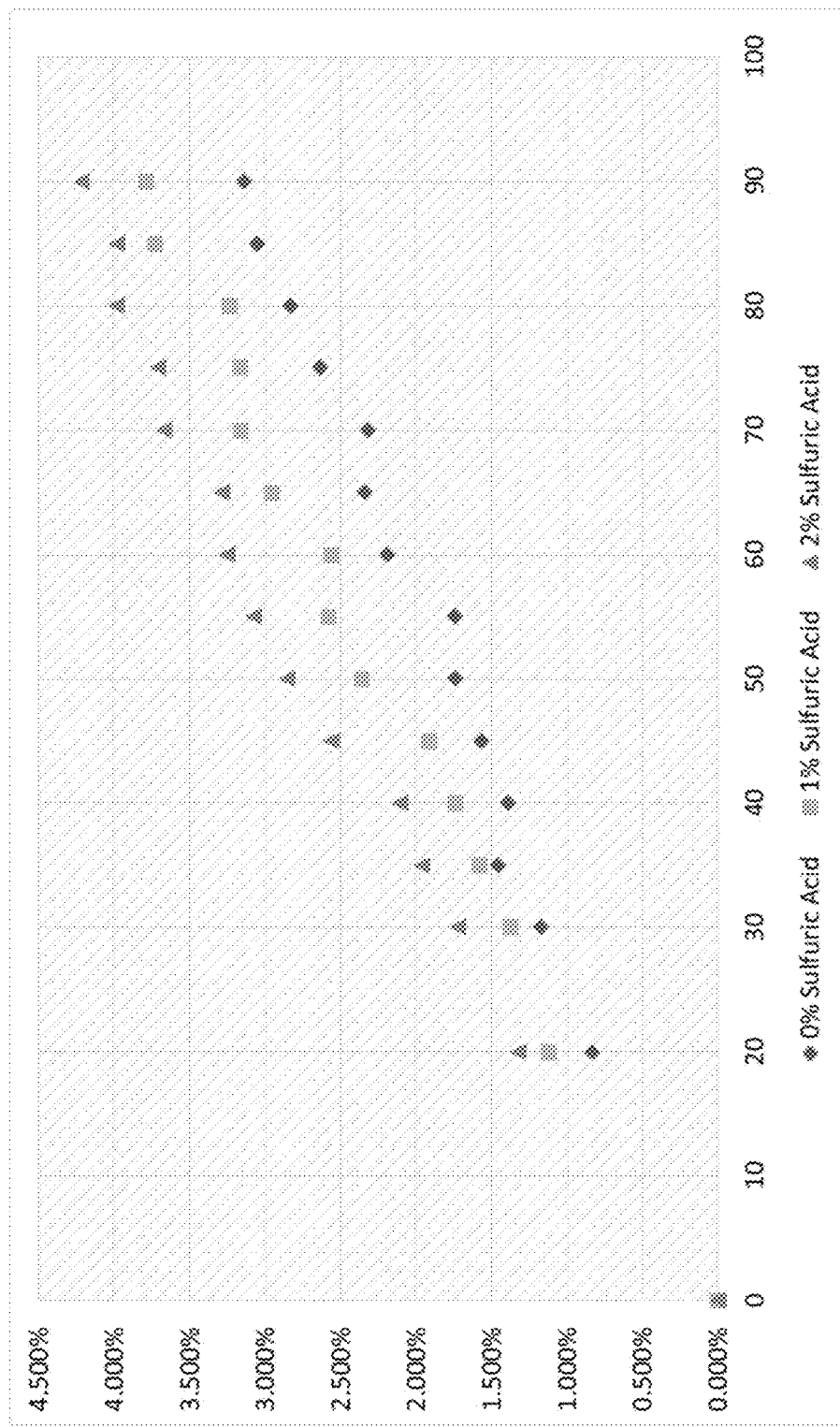
FIG. 2 is a graph showing DFU Formation at 50° C. with varying concentrations of sulfuric acid in accordance with the present invention.

The results of this testing is provided in FIG. 1 and FIG. 2. FIG. 1 shows a graph comparing DFU Formation at 30° C. with varying concentrations of sulfuric acid. FIG. 2 shows a graph comparing DFU Formation at 50° C. with varying concentrations of Sulfuric Acid.

Example 4-8 (6% Sulfuric Acid)

3.62 grams of urea (60.3 mmol), 5.78 g of formic acid, and 0.59 g of 99% varying acids were combined and heated over a period of 3 h at 50° C. Aliquots were taken out at 30 min intervals for analysis.

Figure 3:
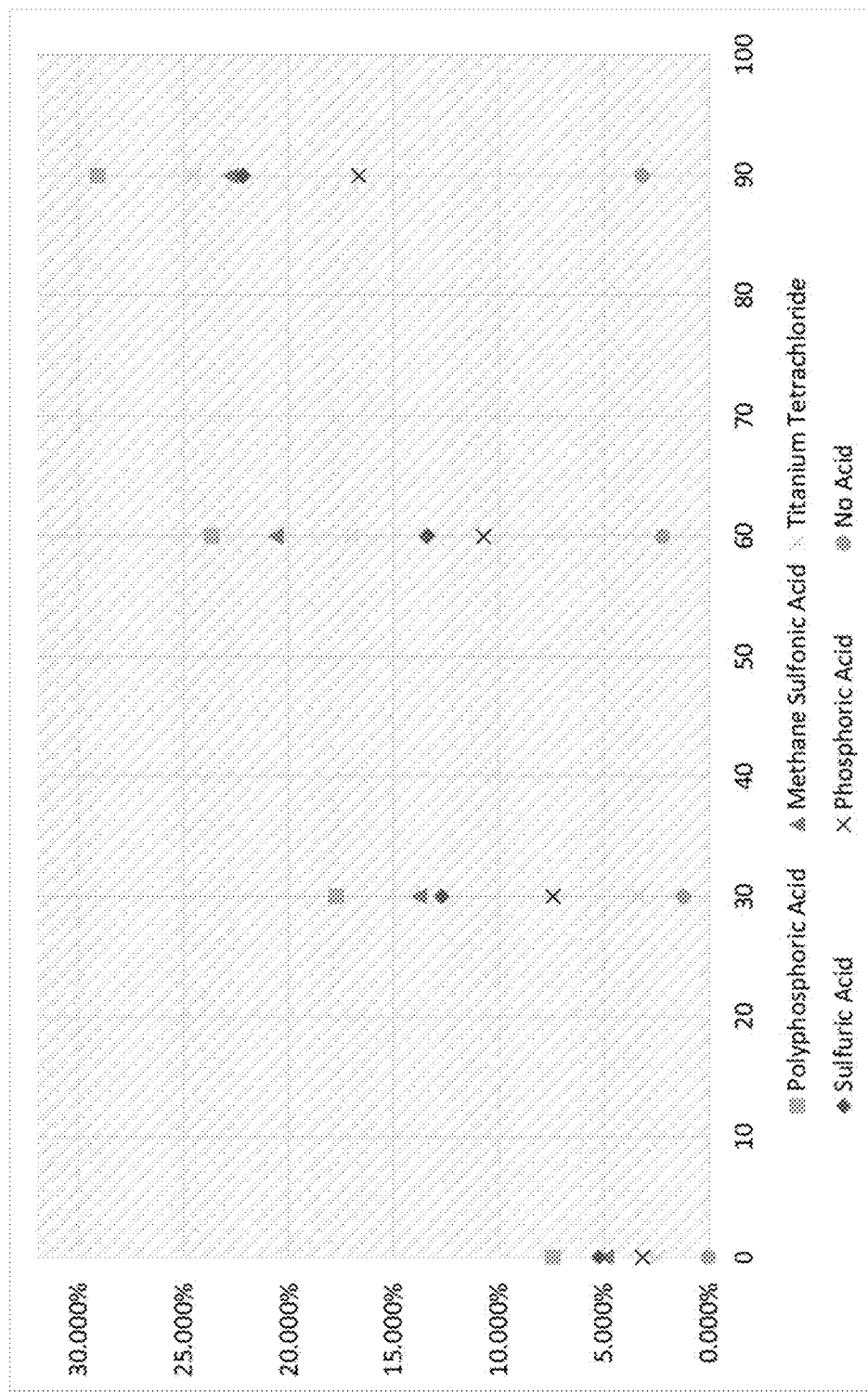
FIG. 3 is a graph showing DFU Formation at 50° C. with 6% concentrations of varying acids in accordance with the present invention.

FIG. 3 compares DFU Formation at 50° C. with 6% concentrations of varying acids.

As shown in FIGS. 1-3, the addition of acid increases the rate of DFU formation.

Figure 4:
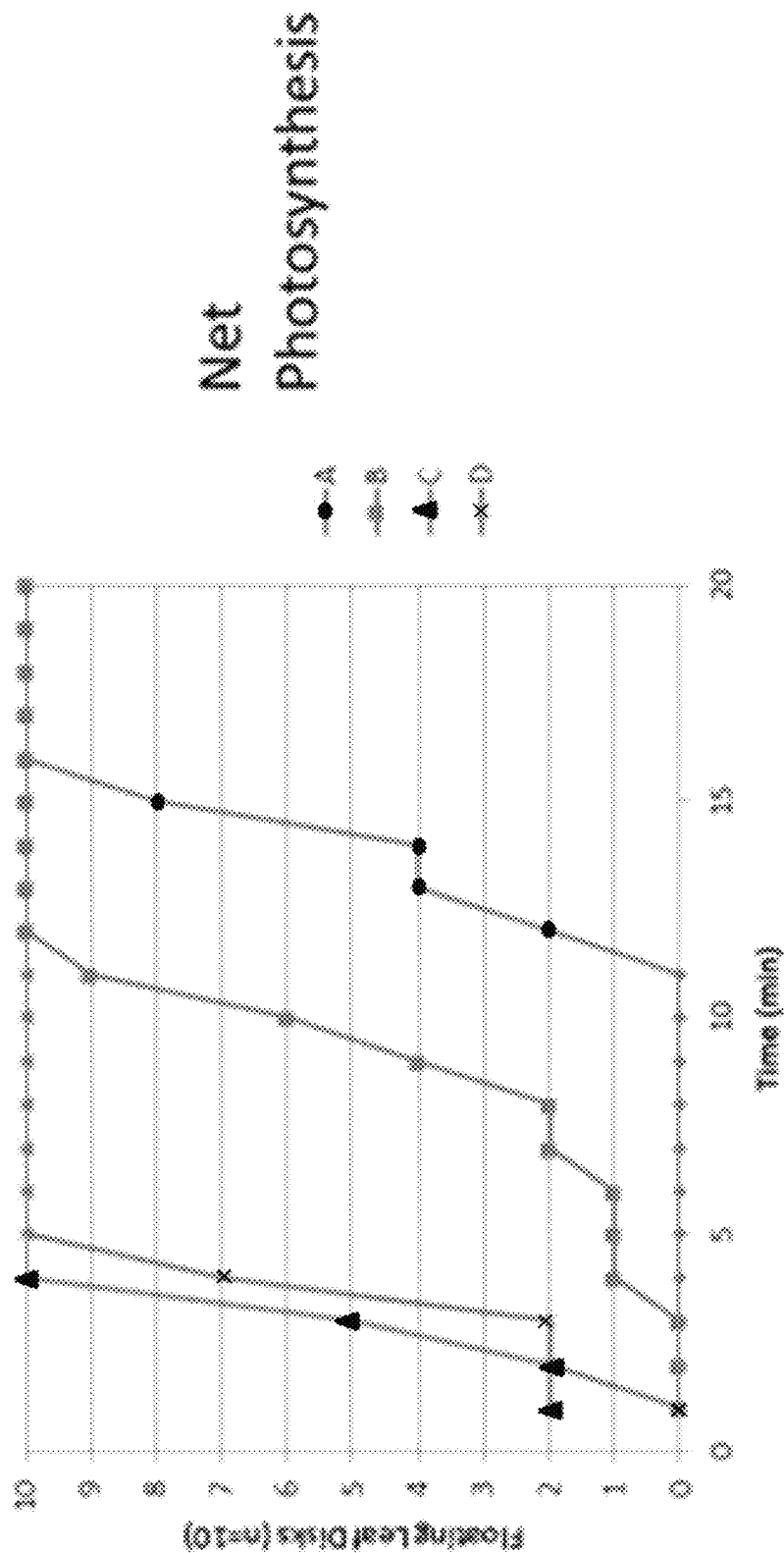
FIG. 4 is a graph showing an example of enhancement to photosynthesis rate via floating leaf disk assay in accordance with the present invention.

FIG. 4 is a graph showing an example of enhancement to photosynthesis rate via floating leaf disk assay. Based on Brad Williamson's Floating Disk Assay for Investigating Photosynthesis, net photosynthesis was evaluated. The assays use the principle that Leaf disks normally float. When the air spaces are infiltrated with solution the overall density of the leaf disk increases and the disk sinks. When the infiltration solution includes a small amount of sodium bicarbonate (baking soda), the bicarbonate ions can serve as a carbon source for photosynthesis. As photosynthesis proceeds oxygen is released into the interior of the leaf which changes the buoyancy—causing the disks to rise. Since cellular respiration, which consumes oxygen, is taking place at the same time, the rate that the disks rises to the top of the solution is a measurement of the net rate of photosynthesis.

As observed in FIG. 4, a single application of the inventive N,N'-diformylurea prepared in the presence of acid (C, D) to Pothos plants increased the photosynthesis rate by about three times over prior formulations including the N,N'-diformylurea (B) without the addition of acid to the reaction solution and five times over control (A). The N,N'-diformylurea (B) formulation includes potassium hydroxide. The inventive N,N'-diformylurea (C, D) formulation contains acid and does not include the addition of potassium hydroxide. The inventive N,N'-diformylurea (C, D) formulation includes N-methyl pyrrolidone (NMP) as a solvent, preferably without the addition of water. It should be understood that other solvents suitable for the agricultural industry may be used in the formulation including, but not limited to, dimethyl sulfoxide (DMSO). Preferably, inventive formulations C and D are beneficially applied to the plant using a formulation that does not include pH modifiers.

Figure 5:
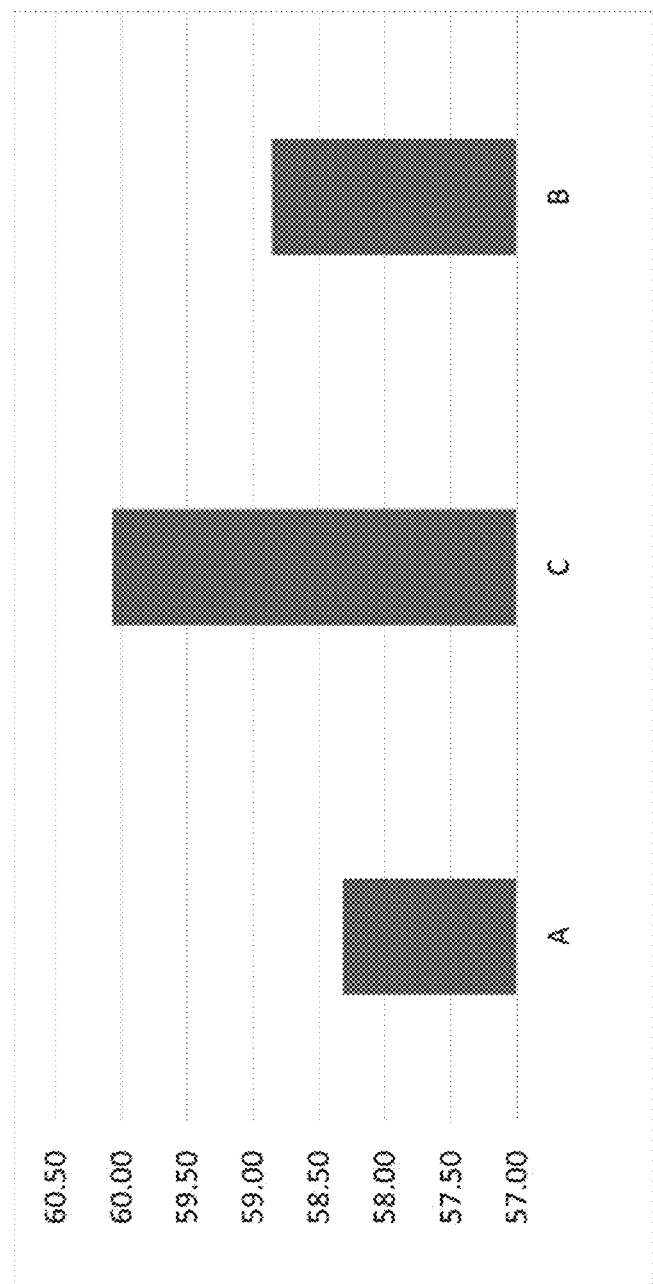
FIG. 5 is a graph showing example of soybean yield enhancement at 2 Ounces/cwt in accordance with the present invention.
Figure 6:
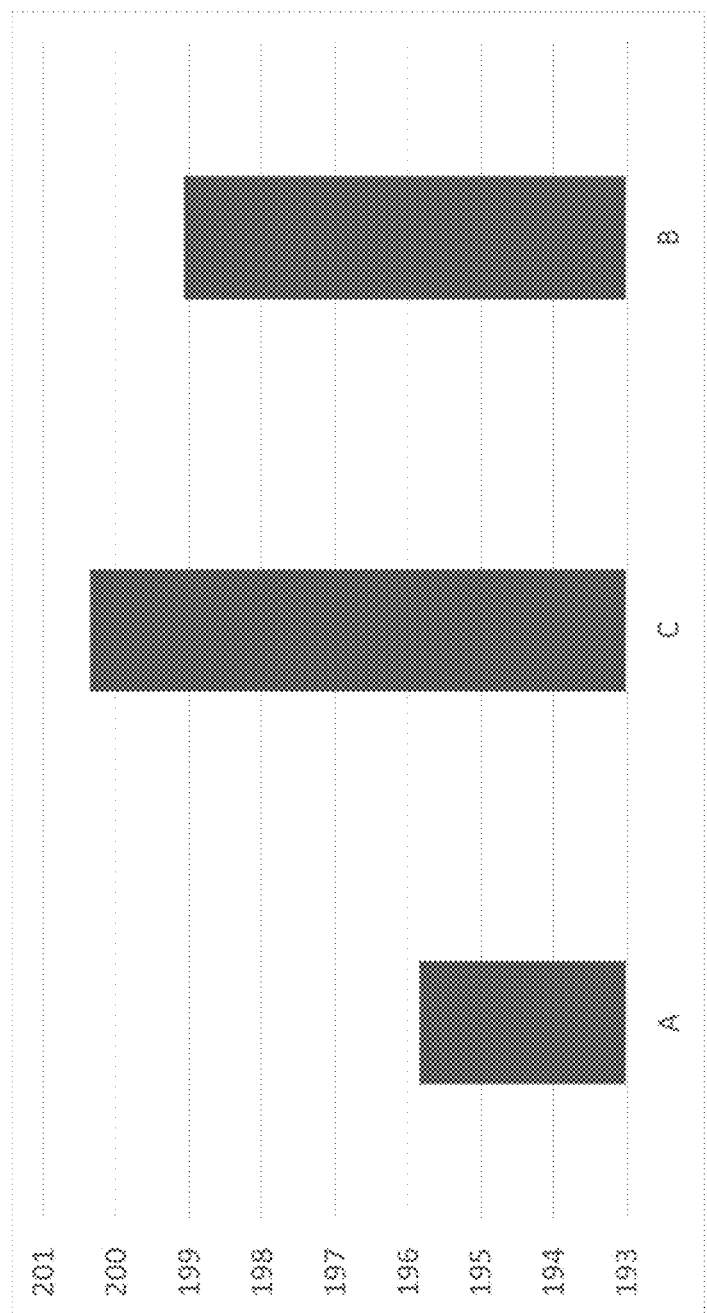
FIG. 6 is a graph showing example of corn yield enhancement at 2 Ounces/cwt in accordance with the present invention.

As observed in FIGS. 5 and 6, 2015 IPSA Seed Enhancement Trials done using 2 ounce/cwt with 4 replications performed at 11 sites in the United States, demonstrated significant yield increases in both a monocot and dicot. The data complements the photosynthesis rate improvement seen with C. FIG. 5 is a graph showing an example of Soybean Yield Enhancement at 2 Ounces/cwt. FIG. 6 is a graph showing an example of Corn Yield Enhancement at 2 Ounces/cwt. As provided above, Sample A is the control, Sample B has no acid added, and Sample C is the inventive formulation including acid.

Figure 7:
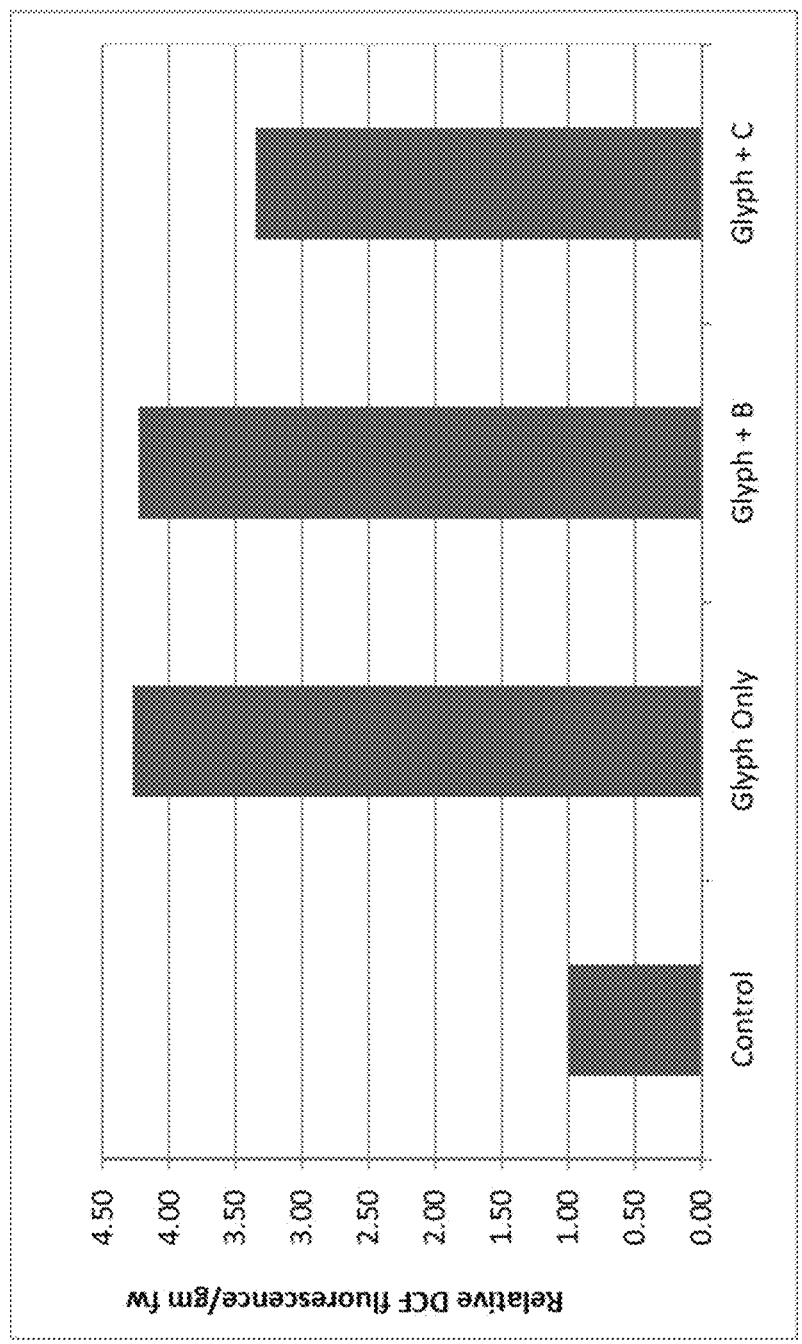
FIG. 7 is a graph showing an example of ROS Reduction Following Glyphosate Stress in accordance with the present invention.

FIG. 7 is a graph showing an example of ROS Reduction Following Glyphosate Stress. As demonstrated in FIG. 7, the N,N'-diformylurea (B) without the addition of acid reduces stress from Glyphosate, a herbicide. Furthermore, inventive N,N'-diformylurea (C) formulation containing acid significantly reduces stress.

The foregoing description of the invention has been directed in primary part to particularly preferred embodiments in accord with the requirements of the Patent Statute and for purposes of explanation and illustration. It will be apparent, however, to those skilled in the art that many modifications and changes in the specifically described invention may be made without departing from the true scope and spirit of the invention. For example, while most of the work reported herein employs diformylurea, other N,N'-di-substituted ureas comprising the reaction product of carboxylic acids and urea in the presence of acid may also be found to provide improved results. Further, those skilled in the art will be aware that the concentration of reaction product in aqueous and/or organic solvents may be adjusted as required based upon the nature of each crop or the application equipment. Therefore, the invention is not restricted to the preferred embodiments described and illustrated but covers all modifications which may fall within the scope of the following claims.

What is claimed is:

1. A method for making a reaction product with enhanced rate of formation comprising
providing a solution including an acyl carboxylic acid and a urea;
adding at least one acid to said solution to form a reaction product having the formula

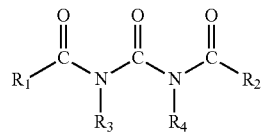

where $R_1$ and $R_2$ are the same or different and selected from the group consisting of H or alkyl and $R_3$ and $R_4$ are the same or different and are selected from the group consisting of hydrogen, substituted and unsubstituted alkyl, allyl, vinyl and alkoxyl groups having from 1-6 carbon atoms, substituted and unsubstituted phenyl groups and the halides,
whereby said reaction product improves plant yield or plant health or both when compared to reactions products made without said at least one acid.

2. The method of claim 1 wherein said carboxylic acid is formic acid.

3. The method of claim 1 wherein said carboxylic acid has the formula RCOOH where R is selected from the group consisting of hydrogen, substituted and unsubstituted alkyl, allyl, vinyl and alkoxyl groups having from 1 to 6 carbon atoms, substituted and unsubstituted phenyl groups and the halides.

4. The method of claim 1 wherein said urea has the formula $(NHR')_2CO$ where each R' is the same or different and is selected from the group consisting of hydrogen, substituted and unsubstituted alkyl groups having from 1 to 6 carbon atoms, substituted and unsubstituted alkoxyl groups having from 1 to 6 carbon atoms, substituted and unsubstituted phenyl groups and the halides.

5. The method of claim 1, wherein said solution includes 0.1-20 wt. % of said at least one acid.

6. The method of claim 1, wherein said solution includes 0.1-10 wt. % of said at least one acid.

7. The method of claim 1, wherein a reaction product N,N'-diformylurea is formed by providing a solution including formic acid as said carboxylic acid and urea as said urea.

8. The method of claim 1, wherein said at least one acid is selected from the group consisting of sulfuric acid, sulfamic acid, hydrochloric acid, hydrobromic acid, hydrofluoric acid, nitric acid, phosphoric acid, polyphosphoric acid, metal halides, alkyl and aryl sulfonic acids, amino acids, trihaloalkyl acids, and organo titanates.

9. The method of claim 1, wherein said at least one acid is selected from the group consisting of polyphosphoric acid, methane sulfonic acid, titanium tetrachloride, sulfuric acid, and phosphoric acid.

10. The method of claim 1, wherein said at least one acid is sulfuric acid.

11. The method of claim 1, wherein said at least one acid is selected from the group consisting of sulfuric acid, sulfamic acid, hydrochloric acid, hydrobromic acid, hydrofluoric acid, nitric acid, phosphoric acid, polyphosphoric acid, metal halides, alkyl and aryl sulfonic acids, trihaloalkyl acids, and organo titanates.

12. The method of claim 1, wherein said carboxylic acid is formic acid, said urea is urea, and said at least one acid is selected from the group consisting polyphosphoric acid, methane sulfonic acid, titanium tetrachloride, sulfuric acid, and phosphoric acid.

13. The method of claim 12, wherein said at least one acid is sulfuric acid.

* * * * *